United States Patent [19]

Semrad

[11] Patent Number: 5,059,183

[45] Date of Patent: Oct. 22, 1991

[54] STOP GUIDE WIRE AND DOUBLE ENDED OBTURATOR-CATHETER-SHEATH SYSTEM AND METHOD OF USE OF SAME

[76] Inventor: Neal Semrad, 2180 Cedarhurst Dr., Los Angeles, Calif. 90027

[21] Appl. No.: 402,343

[22] Filed: Sep. 1, 1989

[51] Int. Cl.$^5$ .............................................. A61M 5/178
[52] U.S. Cl. ..................................... 604/158; 604/165; 604/264; 604/280; 128/772
[58] Field of Search ............... 604/158, 164, 165, 170, 604/264, 280; 128/657, 658, 772

[56] References Cited

U.S. PATENT DOCUMENTS

| | | | |
|---|---|---|---|
| 4,535,773 | 8/1985 | Yoon .................................. | 604/169 |
| 4,616,653 | 10/1986 | Samson et al. ..................... | 128/657 |
| 4,636,200 | 1/1987 | Vaillancourt ....................... | 128/657 |
| 4,650,472 | 3/1987 | Bates ................................. | 604/165 |
| 4,659,328 | 4/1987 | Potter et al. ...................... | 128/772 |
| 4,931,042 | 6/1990 | Holmes et al. .................... | 604/164 |

Primary Examiner—Stephen C. Pellegrino
Assistant Examiner—Michael Rafa
Attorney, Agent, or Firm—Wagner & Middlebrook

[57] ABSTRACT

A guide wire/obturator catheter system for minimizing the possibility of cavity back wall penetration is disclosed. The device is provided with tactile and visual indications of obturator and catheter positioning within the cavity to aid in the precise placement. Another embodiment provides a functionally double-ended obturator which is a trocar when needed and tapered when needed.

8 Claims, 7 Drawing Sheets

FIG. 10A TROCAR COVERED BY TAPER (SOFT TISSUE)

FIG. 10B TROCAR PARTIALLY COVERED BY TAPER (FIRMER TISSUE)

FIG. 10C TROCAR FULLY EXTENDED (DENSE TISSUE)

STOP GUIDE WIRE AND DOUBLE ENDED OBTURATOR-CATHETER-SHEATH SYSTEM AND METHOD OF USE OF SAME

BACKGROUND OF THE INVENTION

Percutaneous catheter placement via guide wires has been in use in the medical field in the United States of America since at least 1979.(A) Indications and procedures for use of guide wire catheter now are employed in a variety of surgical specialties and sub-specialties. Urologists, gynecologists, generalists, chronic disease, hospice and even cardiac surgeons are becoming increasingly involved in its use.(B–E) The drainage of intraabdominal or retroperitoneal cavities or organs, in the debilitated or non-debilitated via the percutaneous route, has largely remained within the purview of the radiologist, as these procedures are usually performed with simultaneous or concurrent internal imaging and effective imaging is essential to drainage of these cavities. Additionally, endoscopic guided procedures such as percutaneous gastrostomy (F) and peritoneoscopy (G) are becoming more common in other non-surgical specialties, as well.

Percutaneous procedures via guide wires for access to the pleural cavity, urinary bladder, the stomach, kidney or abscess may not, initially appear similar. They do, however, share two important facts. First, the properties of the fascia, peritoneal cavity and other intra- or retro-peritoneal structures complicate accurate, safe, comfortable percutaneous procedures through tissue layers. Second, once these layers are traversed while avoiding nearby "obstacles", it is crucial that one cavity wall be penetrated, with all care taken to avoid perforating the "back wall".

Being the most frequently performed invasive transabdominal gynecologic procedure,(H) laparoscopy has remained a little changed technique since first described in English texts in the late 1960's.(I) Indications continue to become more widespread to include possible utility in the diagnosis of appendicitis (J), as well as the surgical therapy, not merely diagnosis, of acute ectopic tubal pregnancies.(K) In such procedures, it is essential that laparoscopic trocar insertion also needs care to avoid penetrating or damaging the back wall, i.e., intraabdominal viscera, perforation after traversing the anterior abdominal wall layers.

After the technique of using the guide wire, access catheter sheath was described for other than small to medium sized vessels, (L) and also described in my U.S. Pat. No. 4,813,929, issued Mar. 21, 1989, the utility of applying this approach to various clinical needs became apparent to me. I became sure that the technique could be applied to a variety of intracorporal cavities, provided some type of either indication of the proximity of the "back wall" or a positive protection against its penetration is provided.

Since Lunderquist first described the use of a guide wire in a transhepatic cholangiogram in 1979, (A), above, a variety of guide wire designs have been developed. They include heavy duty version (M), a super stiff one, (N) a stiff fine design, (O), a movable core modified (P), a new torque version (Q), a modified Lunderquist form (R), a double ended configuration (S), a stiff version with a floppy tip (T), a newer floppy tip (U), a variable length J shape (V), a double ended curved form (W) and even extensions (X) have all been described in the literature identified at the end of this specification with corresponding parenthetically enclosed capital letters. They have been of various alloys including platinum (Y), as well as plastic coated (Z). Various diagnostic and therapeutic maneuvers have been described including shaping the guide wire (AA), a double guide wire technique (BB), stiffening Hickman catheters for cut-down insertion (CC), and even 10 passing from the renal pelvis out the urethra for ureteral catheter placement. None have provided for effective sensing or significant protection from penetrating the "back wall".

BRIEF DESCRIPTION OF THE INVENTION

Faced with this state of the art and the need which I recognized, I have developed a guide wire/obturator catheter system which minimizes the possibility of cavity back wall penetration. It further provides tactile and visual indications of obturator and catheter positioning within the cavity to aid in their precise placement. In the use of a cavity such as the stomach which is located beyond several layers of tissue of different density and firmness, I have provided a functionally double-ended obturator which is a trocar when needed and tapered when needed.

In the basic combination, I employ a guide wire with an enlarged distal end providing a stop for an obturator or catheter placed over the guide wire. One form of obturator is double-ended and reversible, one end a trocar and the opposite end tapered. The guide wire may include visual markings at predetermined distances from the stop to provide visual indications of depth of penetration of the guide wire.

In an alternate embodiment of this invention, the functional double-ended obturator includes a trocar end which is normally covered with a retractable tapered obturator end. A spring or other biasing means maintains the trocar cavity for passage through soft tissue and exposed for incising dense or firm tissue.

BRIEF DESCRIPTION OF THE DRAWING

This invention may be more clearly understood from the following description and by reference to the drawing, in which.

DETAILED DESCRIPTION OF THE INVENTION

Figure 1A:
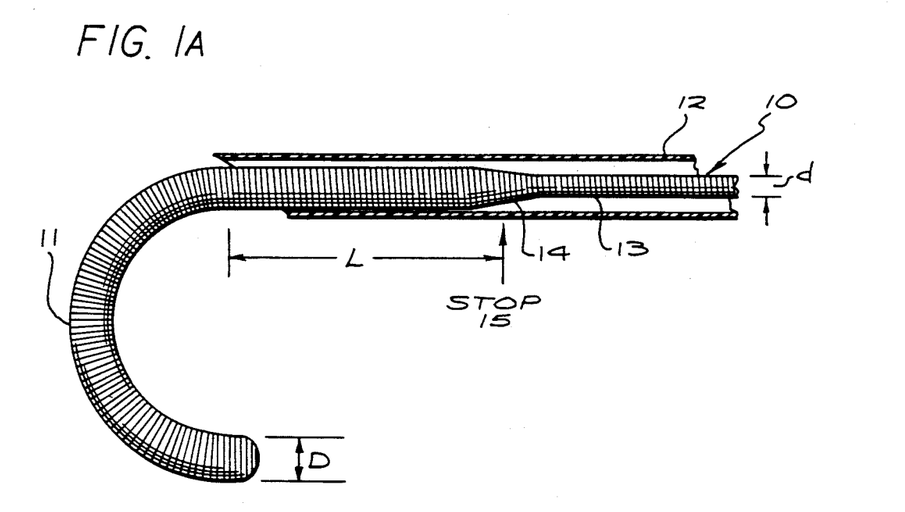
FIG. 1A is a side elevational view partly in section of the distal end of a guide wire and needle incorporating this invention.
Figure 1B:
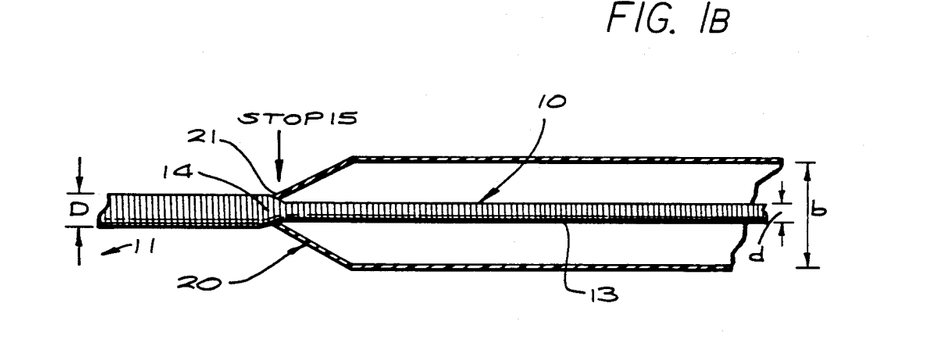
FIG. 1B is a side elevational view partly in section of the guide wire of this invention after removal of the needle of FIG. and insertion of an obturator/internal catheter up to the integral stop of the guide wire.

The preferred embodiment of the stop guide wire and obturator catheter of this invention may best be seen in FIGS. 1A and 1B wherein a guide wire, generally designated 10, includes a distal end 11 in the preferred form having a curved end of a J. The distal end 11 has an outside diameter D which corresponds, with suitable clearance, to the inside diameter or bore of a needle 12 of FIG. 1A which is used for entry into the selected body cavity and for the insertion of the stop guide wire 10. The intermediate portion 13 of the guide wire 10 is of lesser and uniform diameter d and consequently passes freely through the needle 12 bore. A transition region 14 between the distal portion 11 and the intermediate region 13 constitutes a stop 15.

The distal end 11 of the guide wire 10, as shown in FIG. 1A, is soft, floppy and optionally includes the J end as shown. Characteristically, it need be of less stiffness than is required for penetrating the selected body cavity wall. The J end form is preferred and typically the stop guide wire 10 is formed of helical turns of stainless steel various gauge wire with the different diameters and dimensions preferred for particular procedures. In general, the location of the stop 15 will vary with different applications. In vascular access catheter systems, the stop 15 is located adjacent to the J form distal end 11 as illustrated in FIG. 1A. To assure intravascular placement but avoid intimal guide wire induced trauma and/or vessel back wall perforation.

For use in laparoscopy, the stop 15 is more distal to assure intraperitoneal placement of the wire 10 and, after being stopped immediately following intra-abdominal penetration, the stop guide wire 10 and a trocar can be more carefully advanced, if needed.

Below are examples of various procedures and recommended dimensions and stiffness for the guide wire of this invention.

| PROCEDURE | DIA. D | DIA. d | LENGTHS 11, 14, L | STIFFNESS |
|---|---|---|---|---|
| Vascular Access | 23–8 ga | 26–10 ga | 1–3 cm, .1–.5 cm, .1 cm | pliable to stiff |
| Central Nervous (intracranial/ spinal column access) | 23–6 ga | 26–10 ga | 1–3 cm, .1–.5 cm .1 cm | pliable to stiff |
| Laparoscopy | .5–2 cm | .25–1.75 mm | 3–5 cm, .5–1 cm | stiff (distal) |

-continued

| PROCEDURE | DIA. D | DIA. d | LENGTHS 11, 14, L | STIFFNESS |
|---|---|---|---|---|
| Percutaneous Gastrostomy | 8–22 ga | 10–26 ga | 10 cm 1–3 cm .25 cm, 1–3 cm | moderate |
| Urinary Cystostomy | 8–22 ga | 10–26 ga | 1–3 cm, .25–.5 cm 1–3 cm | moderate |
| Percutaneous Nephrostomy | 8–22 ga | 10–26 ga | 1 cm, .25–.5 cm .5–1 cm | more stiff |
| Abscess cavity drainage | 8–22 ga | 10–26 g | 1 cm, .1–.5 cm .25–1 cm | very pliable |

The stop guide wire 10 of this invention is used with an obturator/internal catheter 20 of the type illustrated in FIG. 1B. Characteristic of the obturator/internal catheter 20 which is significant with respect to the stop guide wire 10 is the fact that its internal bore b is greater than the diameter d of the intermediate portion 13 and includes an orifice in its trocar end 21 which is of lesser diameter than the distal end diameter D of the stop guide wire 10. With this dimensional relationship, the distal end of the obturator/internal catheter can proceed no further than the stop 15 and is incapable of penetrating any tissue beyond that penetrated by the guide wire 10.

Figure 2:
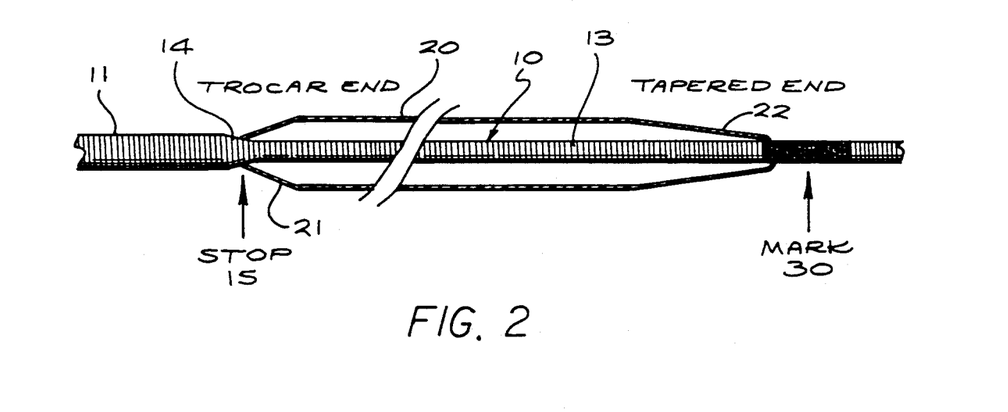
FIG. 2 is a side elevational view, partly in section, of guide wire including an integral stop and marking with a double ended obturator/internal catheter.
Figure 3:
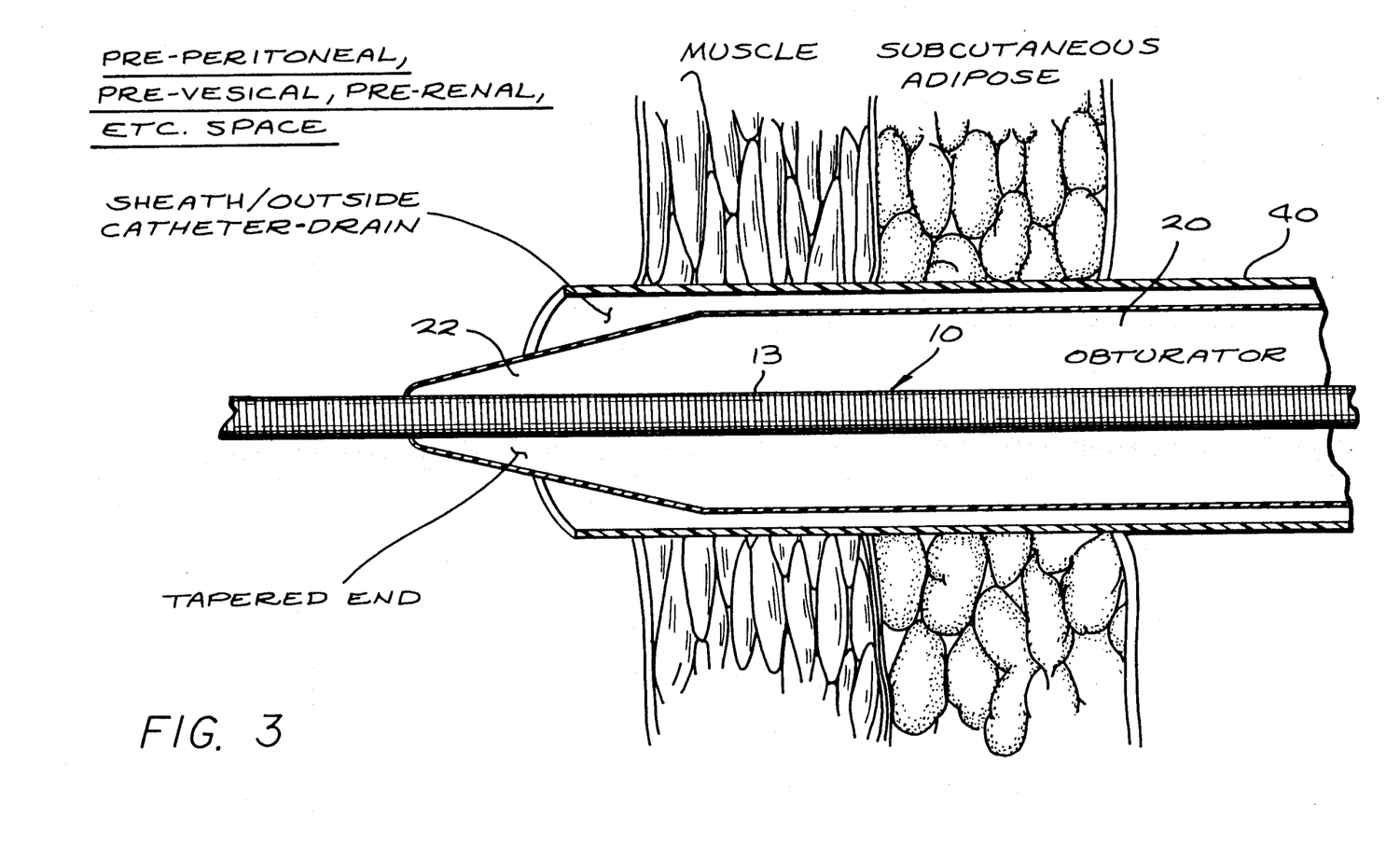
FIG. 3 is an enlarged sectional view through the wall of a patient's cavity with multiple layers of tissue showing the double ended obturator of this invention in place with the tapered end entering the cavity surrounded by a sheath/outside catheter-drain all on a stop wire of this invention.
Figure 6:
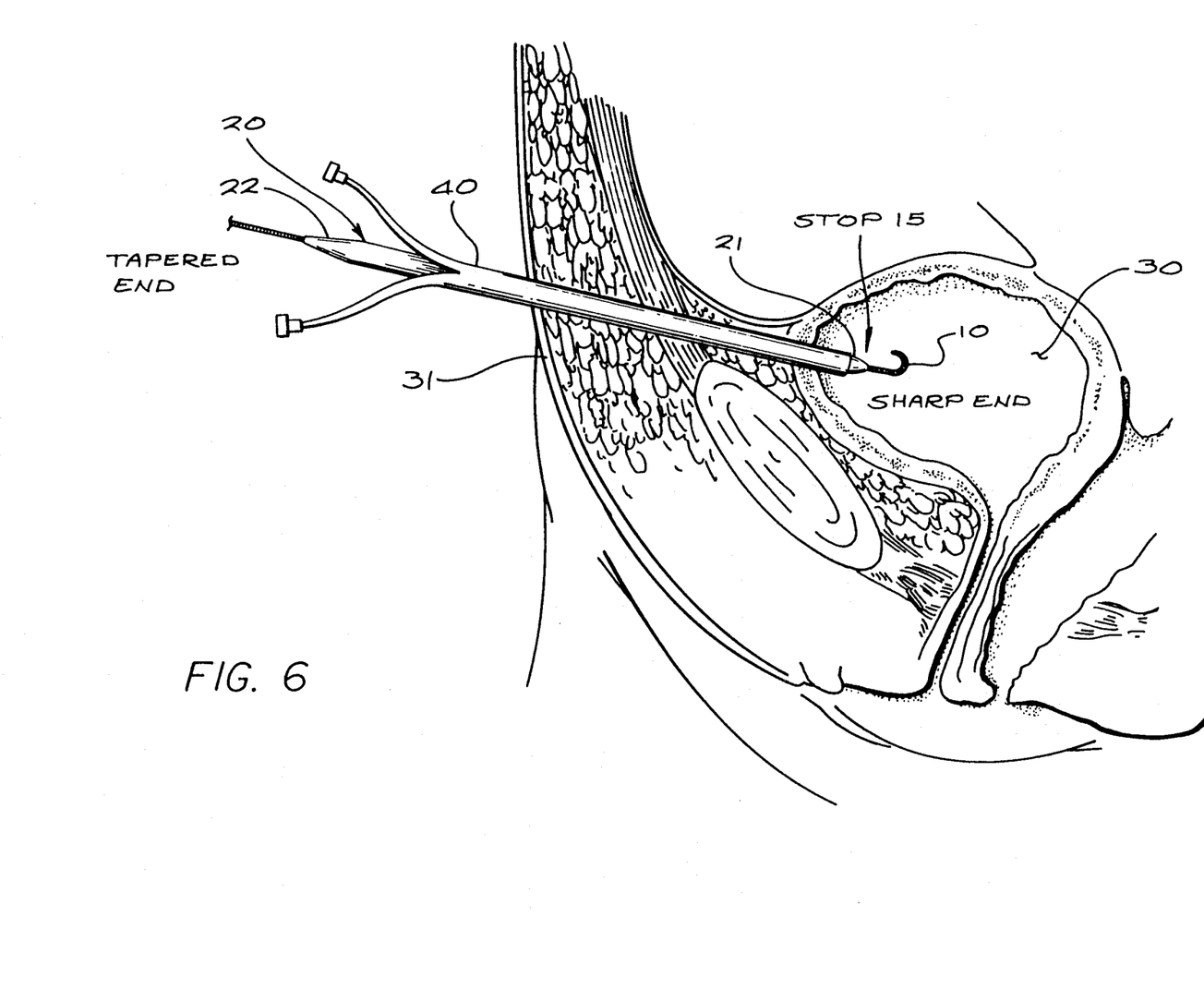
FIG. 6 is a sectional view through the urinary portions of a patient with the stop guide wire, double ended obturator and catheter sheath in place with the trocar end of the obturator bearing against the stop of the guide wire.

The obturator/internal catheter 20 additionally has a tapered end 22, opposite from the trocar end 21, as illustrated in FIGS. 2 and 3 in section, and in FIG. 6, where the obturator 20 is shown in place during a percutaneous urinary tube placement.

A comparison of the trocar and tapered ends of the obturator 20 may be made particularly by reference to FIG. 2 in which both ends are shown in section and clearly identified. FIG. 2 further illustrates the feature of this invention by which the intermediate portion 13 of the guide wire 10 includes a mark 30 which may be a dye or surface coating of the wire making up the stop guide wire 10. The mark is so positioned on guide wire 10 with respect to the stop 15 and the length of the trocar 20 that the operator knows precisely the relative position of the opening in the internal end of the obturator 20 in the sample shown in FIG. 2, the mark may extend for a few millimeters and as soon as the mark appears out of the orifice in the outboard end of the obturator 20, the physician knows that the inboard end is approaching the stop 15. Thus the position of the mark is correlated to a particular guide wire and trocar combination. Of course, multiple marks of different colors, for example, may be used with different length obturator.

The obturator 20 of FIG. 3 is used as illustrated in that figure with its trocar end 21 forward for penetration of tough abdominal muscular tissue or may be reversed with the tapered end forward for passage through soft tissues as is encountered in the pre- and retro-periteneum. The normal procedure is to use the obturator 20 with its trocar end 21 forward which easily pierces the fascia and body cavity front wall. The trocar end 21 is limited in penetration by the operator or the stop 15 of guide wire 10. Thereafter the obturator 20 may be withdrawn on the guide wire 10, reversed and reinserted using the tapered end 22 to spread the tissue and enter the body cavity until its end engages the stop 15 of the guide wire 10.

In either case, after the guide wire 10 and obturator 20 have been inserted into the body cavity. with the sheath 40 in place, the guide wire 10, and obturator 20 are removed together. Due to the presence of the stop 15, the guide wire 10 may not be withdrawn without the obturator 20, regardless of its orientation, trocar or tapered end first.

The stop 15 of the transition region 14 further acts as a plug for the orifice at either obturator end until such time that the guide wire 10 is extended further within the body cavity after the obturator/internal catheter 20 is in place.

As is particularly illustrated in FIGS. 1B and 2, the stop 15 aids in preventing back wall perforation of any anatomical or pathophysiologic cavity. Also, it becomes unnecessary to advance excessive lengths of the guide wire 10 into any cavity as has been the practice in the past to insure that the obturator does not go beyond the guide wire tip. The guide wire 10 thus has an intracorporal end point, the stop 15. The rigidity of the guide wire distal and proximal to the stop 15 is varied according to the need from floppy throughout its length to an essentially rigid rod. Various selections are indicated above. It is possible within the concept of this invention that the stop 15 is, in fact, compressible and compressed while within the needle 12 of FIG. 1A and expanded once the distal end of stop wire 10 is within the body cavity and exits the needle introducer 12.

Figure 4:
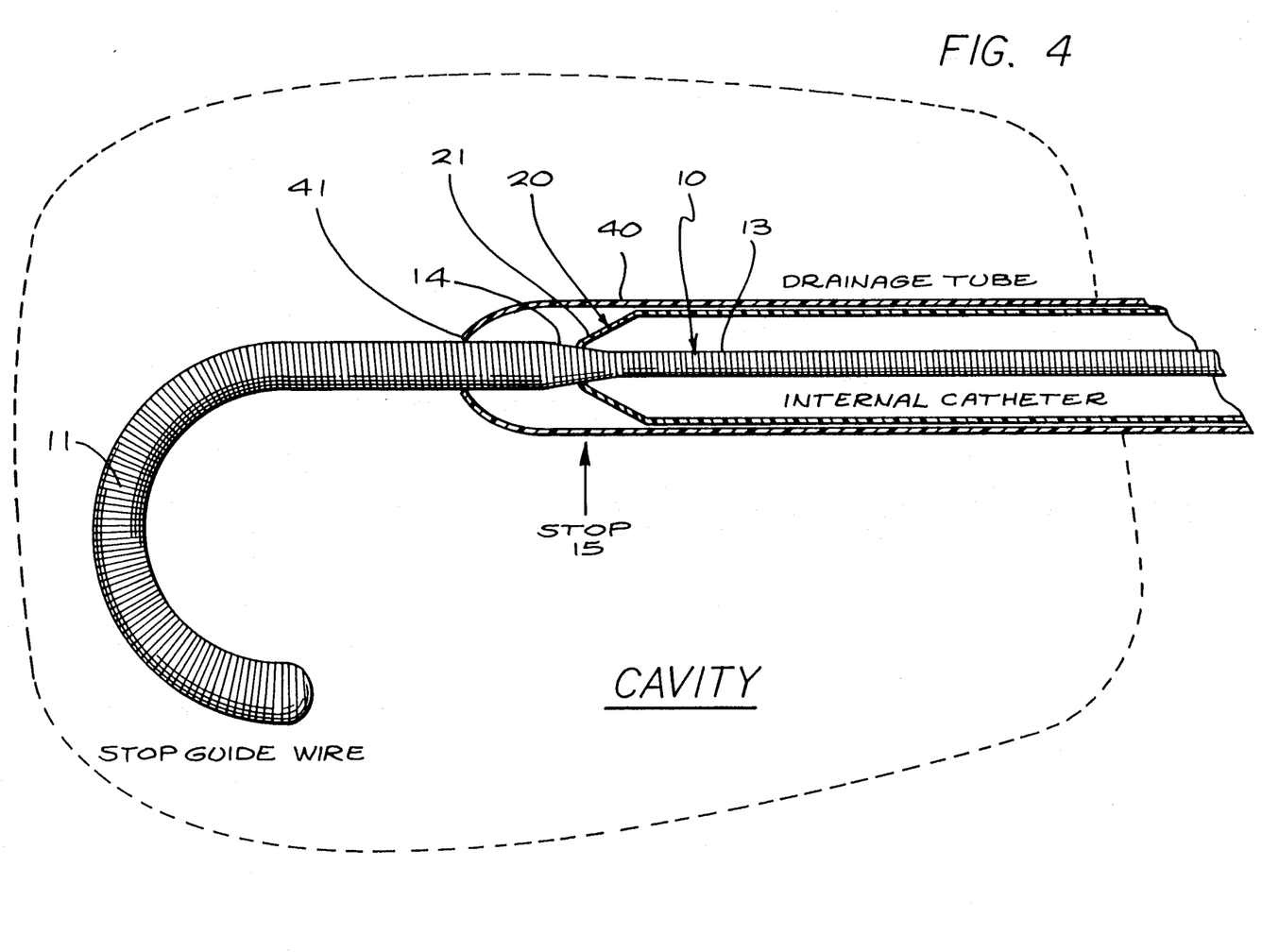
FIG. 4 is a side elevational view of a body cavity with a stop guide wire internal catheter and drainage tube shown partly in section.
Figure 7:
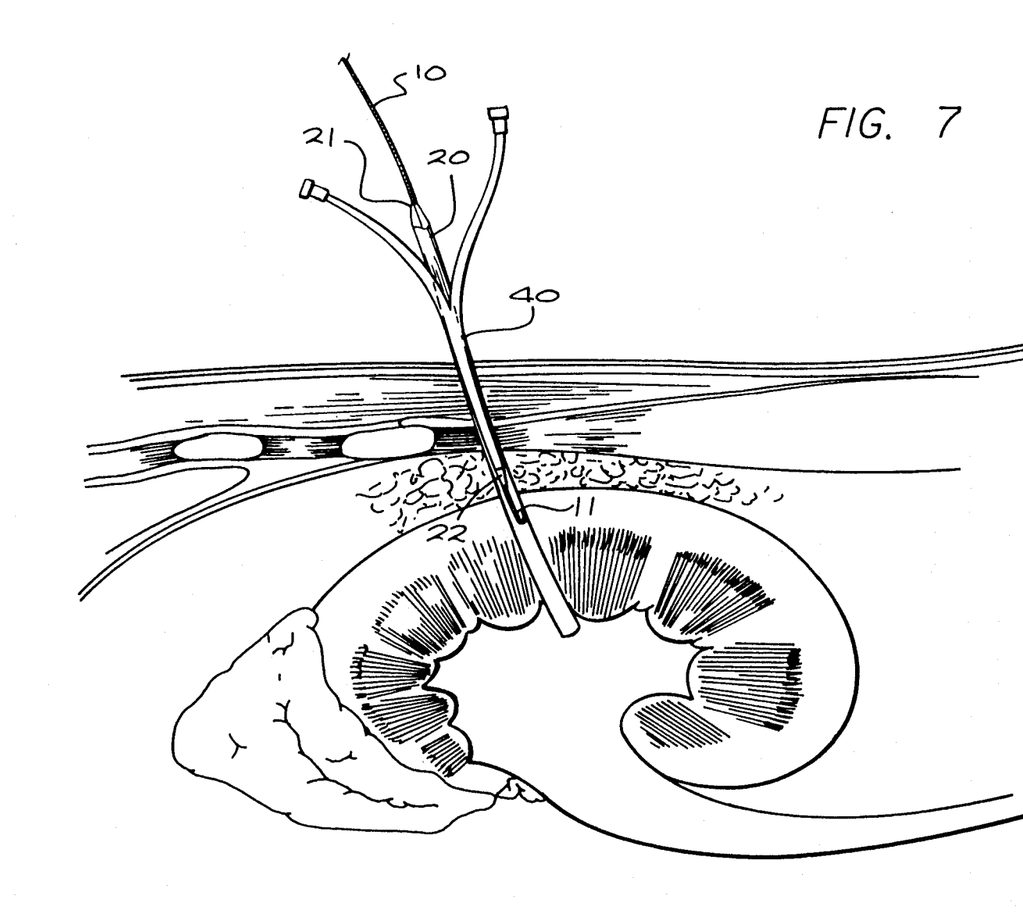
FIG. 7 is a sectional view through the rear muscular area and kidney of a patient showing a catheter in place with the obturator and stop wire being removed together.

For some procedures or situations, an obturator-access catheter sheath of either the split or non-split type may be inappropriate and an internal catheter of various piercing capabilities can be inserted over the guide wire instead. The drainage/installation tube then slides over the outside of the internal catheter after both have been stopped by the guide wire. This is illustrated in FIG. 4 in which the obturator 20 with its trocar end 21 forward has reached for stop 15 in the transition region 14 and can make no further entry into the body cavity. Drainage tube 40 which has slipped over the obturator 20 had reached the stop 15 which is observable by the position and in the case of FIG. 4 the drainage tube 40 being flexible and slightly elastic has been allowed to expand slightly into the distal region 11 employing the flexible nature of the drainage tube 40 in the region of its orifice 41. Using the combination of the stop guide wire 10 with a marking 30 as illustrated in FIG. 2 and the 10 noticeable increase in resistance as the drainage tube has been inserted into the body cavity, the physician knows the precise location of the end of the drainage tube 40. After emplacement as shown in FIG. 4, the stop guide wire and obturator 20 or internal catheter are withdrawn together. Such a step is illustrated in FIG. 7.

Figure 5:
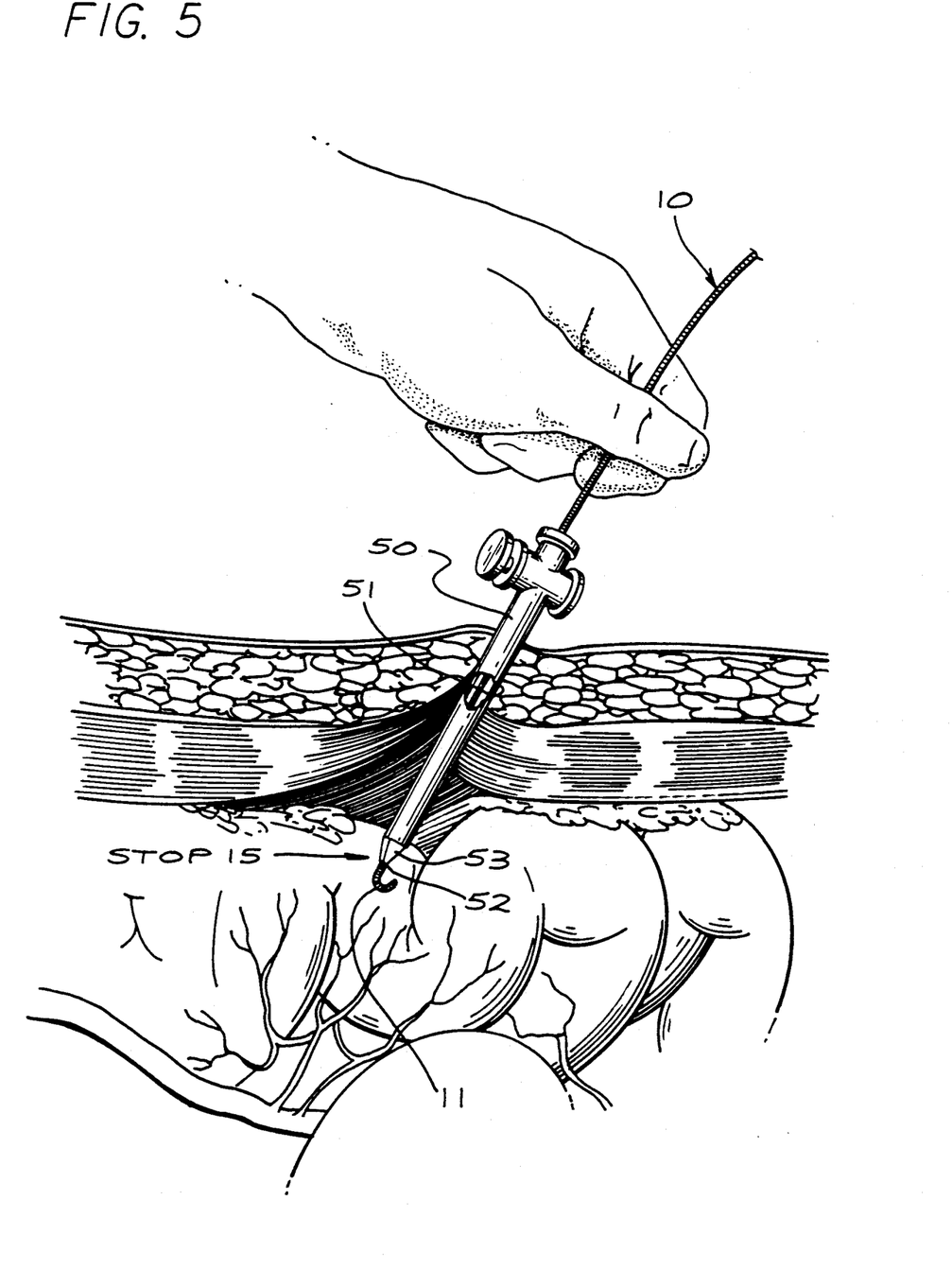
FIG. 5 is a sectional view through the abdomen of a patient with a laparoscopic application of this invention in which a trocar is modified with the central longitudinal hole and a stop guide wire of this invention is shown within trocar.

As illustrated in FIG. 5, this invention may be modified for laparoscopic procedures. In that case, the conventional trocar 50 is modified by the inclusion of a central longitudinal hole shown in the breakaway portion 51 through which the stop guide wire 10 has been inserted from the trocar end with the stop 15 resting against the aperture wall 52 in the trocar end 53. The distal end 11 of stop wire 10 as shown in this case having the common "J" shape. The trocar cutting edge is stopped by the stop 15 and the danger of penetration of intestinal or other organ walls is minimized.

As shown in FIG. 6, the distal end 11 of the guide wire 10 is in the bladder 30 of the patient after penetrating the skin 31, the abdominal muscles and the anterior wall of the bladder 30. The stop 15, at the upper end of the J body has limited the inward penetration of the trocar end 21 of the obturator 20 while its opposite tapered end 22 remains out of the patient's abdomen wall. The obturator 20 is surrounded by sheath 40 which may be of the solid or split end type, the latter of which is shown in FIG. 6.

PROCEDURE The procedure for employing the stop guide wire of this invention is basically as follows:

Following appropriate, usually local or regional, anesthesia, the desired cavity is entered with the stop guide wire-needle combination of FIG. 1A. For urinary cystostomy tube placement, one may enter above the previously irradiated pelvic field and after facial penetration immediately aim inferior and caudal toward the previously filled bladder. Care must be taken to avoid entering the peritoneal cavity for this supra pubic urinary catheter placement. Aspiration of urine/saline assures intra/vesical needle placement and the stop guide wire 10 is delivered through the needle 12. For percutaneous gastrostomy the needle 12 is introduced into the stomach under endoscopic control after transillumination of the stomach and abdominal wall, then the stop guide wire 10 is introduced. Internal imaging the guide needle 12 placement for percutaneous nephrostomy is carried out in the usual manner and then the stop guide wire 10 is introduced, so too for intra-abdominal or retro-peritoneal abscess/cyst drainage.

An increase in flow may be noted as the stop end 15 exits the needle 12 tip leaving the smaller diameter portion of the guide wire in the needle 12. Although the increase flow of fluids may further assure correct needle placement, should continued flow be undesirable, the needle 12 may be immediately withdrawn over the guide wire 10. The smaller caliber portion 13 of the stop guide wire 10 can be passed further, if necessary. The length of the guide wire 10 to be passed with or without the guide wire needle 12 in place, is determined clinically, as well as by guide wire marking 30 of FIG. 2. Again, excessive intra-cavitary lengths are unnecessary due to the stop 15.

After the introducer needle 12 is removed, the obturator access catheter sheath 20 of FIG. 3 or the drainage tube 40 of FIG. 4 is delivered over the guide wire 10 after appropriate skin incision. For most urinary drainage, the obturator access catheter sheath 40 is advanced fully to the stop 15 as illustrated in FIG. 6. One may note flow of fluids around the guide wire 10 via the obturator internal catheter 20 after entering the cavity such as cavity 30 of FIG. 6. As one reaches the stop 15 of the guide wire 10, a clear tug will be felt at the distal end of the guide wire 10. Also, fluid flow may be reduced or stopped, as well. If the guide wire 10 is marked as 30 in FIG. 2, the placing physician will also see that the obturator/internal catheter 20 has reached its full length along the guide wire 10 from the stop point 15 This is best illustrated in FIG. 2.

The obturator 20 and guide wire 10 are then removed together, as the stop guide wire 10 cannot, nor need be, withdrawn through the obturator 20 due to the presence of the stop 15 and appropriate catheter can then be placed through the sheath 40 and the sheath 40 withdrawn and or split away. For most situations including some urinary bladder cystostomy tube placements, the reversal technique using the double ended obturator 20 is used as illustrated in FIG. 3 with the trocar end 21 first used to penetrate the tougher tissues such as muscle and the tapered end replacing the trocar end for penetrating softer tissue.

If the internal catheter 20 with the drainage tube 40 over its outside has been introduced as illustrated in FIG. 4, the drainage tube 40 is advanced slightly and then the internal catheter 20 and stop guide wire 10 are removed as a unit. An example of that removal step is illustrated in FIG. 7 with the J shaped distal end 11 of guide wire 10 partly straightened as the obturator 20 and guide wire 10 are removed together.

ALTERNATE EMBODIMENT

Figures 8, 9:
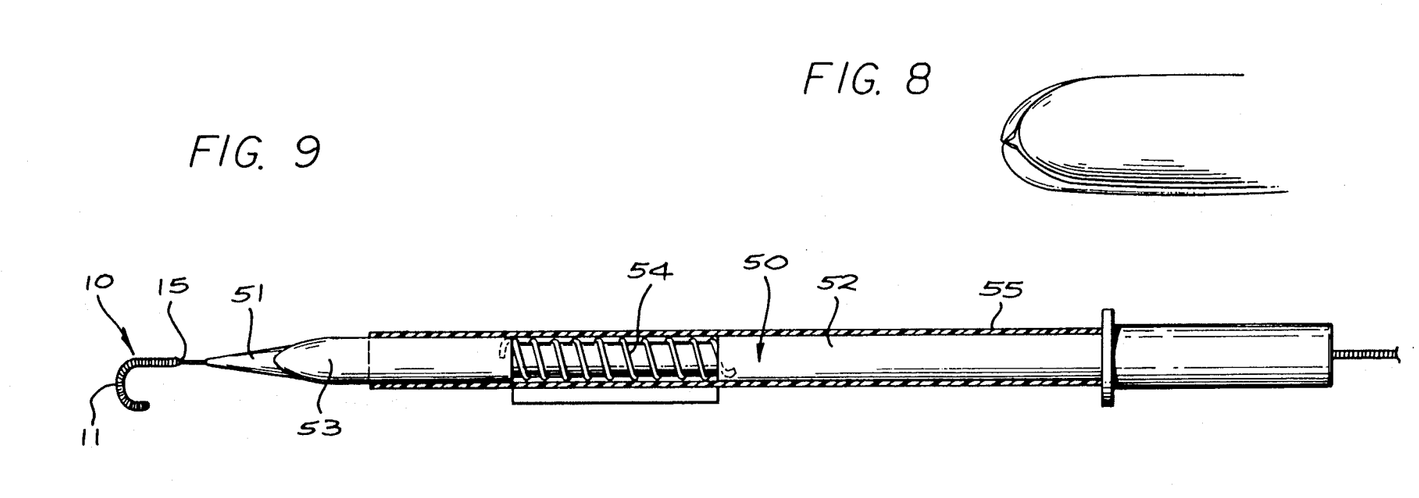
FIG. 8 is a longitudinal partly sectional view of a functional double ended obturator catheter sheath stop wire of this invention.
FIG. 9 is a fragmentary sectional view of the tapered obturator end of the combination of FIG. 8.

The reversible double ended obturator of FIGS. 2 and 6 meet most situations. However, to avoid the need of removal of the obturator its reversal and replacement, I have designed a functionally double ended obturator/catheter/shield which requires no reversal procedure. It is illustrated in FIGS. 8 and 9 to which a reference is now made.

Figure 10A:
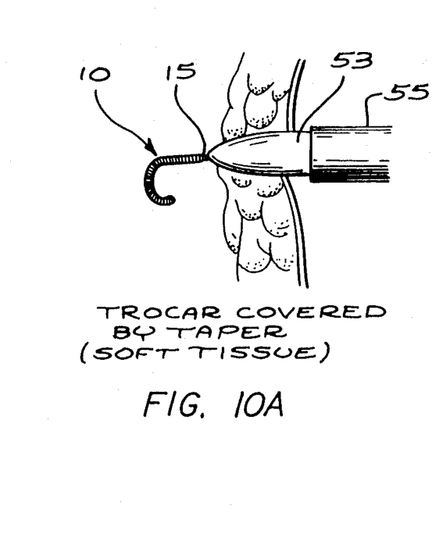
FIGS. 10a–c are vertical sectional views through different types of tissue with the combination of FIG. 9 in the process of penetrating that tissue.
Figure 10B:
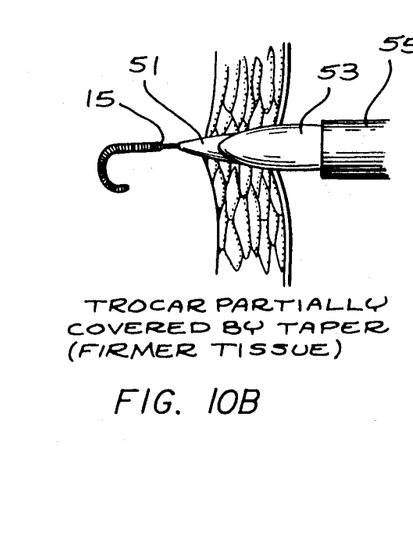
Figure 10C:
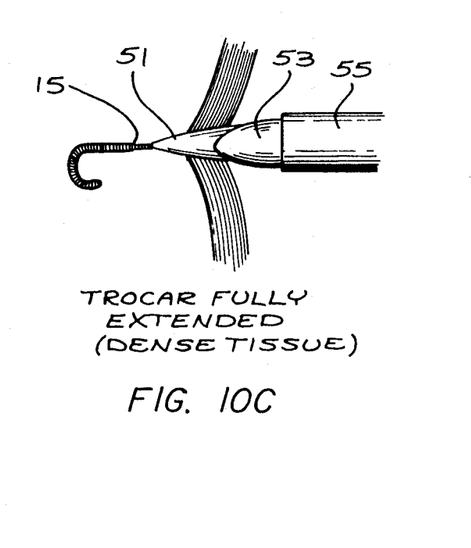

The stop wire guide wire 10 of this invention with its integral stop 15 and its distal end 11, is preferred in this application, particularly, since the obturator 50 at all times includes a trocar 51 which is rigidly applied to the obturator body 52. The trocar 51 however is concealed within the tapered obturator 53 which is spring biased forward or distal direction by an internal spring 54 or other resilient mechanical means. The tapered obturator 53 normally covers the trocar obturator 51 as is illustrated in FIG. 10A during normal passage of soft tissue. If the obturator reached firmer tissue, the tapered obturator 53 is retracted as spring 54 is compressed approximately exposing the trocar obturator 51 for penetrating this firmer tissue. This is illustrated in FIG. 10B. When dense tissue is encountered, the tapered obturator 53 becomes nearly fully depressed exposing the full trocar 51 for penetration through that dense tissue as shown in FIG. 10c. As soon as penetration is achieved, and the body 52 and its outer sleeve or shield 55 penetrates the firmer tissue of FIG. 10C, the tapered obturator returns to its trocar concealing position.

Regardless of the quality of the tissue encountered neither the tapered or the trocar obtruators, can pass beyond the stop 15 and penetration of any cavity rear wall is prevented.

Regardless of whether a single ended obturator, a double ended obturator or a functional double ended obturator is used, the stop guide wire of this invention, serves to provide the operating physician, with indications of the extent of introduction of the obturator into the cavity of interest and reduction of the risk of back wall penetration.

The foregoing constitute the best mode known by the applicant for carrying out this invention; however, the specific embodiments disclosed are illustrative of the principle of the invention and are not limiting in its scope. To the contrary, it is recognized that one of the ordinary skill in the art, given this teaching, may make variations in the structure or compositions without departing from the spirit and scope of the invention. Its scope is defined by the following claims including the protection offered by the doctrine of equivalents.

REFERENCES (A) Lunderquist A., Lunderquist M., Owen T. Guide wire for percutaneous transhepatic cholangiography. Radiology 1979; 132:228.

(B) Sethia K. K., et al. Prospective randomized controlled trial of urethral versus suprapubic catheterization. Br J Surg 1987; 74(F):624–5.

(C) Andersen J. T., et al. Suprapubic versus transurethral bladder drainage after colposuspension/vaginal repair. Acta Obstet Gynecol Scand. 1985; 64(2):139–43.

(D) Kottinen M., et al. Suprapubic cystostomy catheterization in open-heart surgery. Scand J., Thorac Cardiovasc Surg 1984; 18(2):167–8

(E) Shapiro J., Hoffman J., Jersky J. A comparison of suprapubic and transurethral drainage for postoperative urinary retention in general surgical patients. Acta Chir Scand 1982; 148(4):323–7.

(F) Cantor M. C., Miskovitz P. F. Percutaneous Endoscopic Gastrostomy. Infections in Surgery 1988; November:643–653.

(G) Orlando R., et al. Complications of laparoscopy in the elderly: a report on 345 consecutive cases and comparison with a younger population. Endoscopy 1987; 19(3):145–6.

(H) Yuzpe A. A. The past, the present and the future: The 1985 AAGL presidential address. J Repro Med 1986; 31(7):573–6

(I) Bordahl P. E. Tubal sterilization: a historical review. J Repro Med 1985; 30(1):18–23.

(J) Whitworth C. M., et al. Value of diagnostic laparoscopy in young women with possible appendicitis. Surg Gynecol Obstet 1988; 167:187–190.

(K) Brumsted J., et al. A Comparison of laparoscopy and laparotomy for the treatment of ectopic pregnancy. Obstet Gynecol 988; 716:889–92.

(L) Semrad N. A new technique for closed thoracostomy insertion of chest tube. Surg Gynecol Obstet 1988; 166:171–3.

(M) Butto F., et al. New heavy-duty exchange guide wire. Radiology 1987; 163:276–8.

(N) Smith T. P., et al. New super-stiff guide wire. Radiology 1986; 161:551–2.

(O) Cope C. Stiff fine-needle guide wire for catheterization and drainage. Radiology 1983; 147:264.

(P) Smith T. P., et al. Movable core guide wire: evaluation of improved model. Radiology 1986; 159:552–3.

(Q) Robinson J. D., et al. A new torque guide wire. Radiology 1987; 165:572–3.

(R) Wikholm G. Use of a modified Lunderquist guide wire for (S) Kadir S. A multipurpose, double-ended guide wire. AJR 1984; 143:626.

(T) Cordella J. F., et al. Very stiff guide wire with a floppy tip. Radiology 1985; 156:837.

(U) Coons H.G. A floppy-tipped wire guide for interventional procedures. AJR 1985; 144–254.

(V) Hawkins, Jr., I. F., Hawkins M. C. New coaxial exchange guide wire with a variable-length tip. Radiology 1985; 148:330–4.

(W) Horton J. A. A doubly curved guide wire for use in the subclavian/vertebral artery system. Radiology 1985; 157:262.

(X) Cope C. Guide wire extension. Radiology 1985; 157:203.

(Y) Meyerovitz M. F., Levin D. C., Boxt L. M. Superselective catheterization of small-caliber arteries with a new high-visibility steerable guide wire. AJR 1985; 144:785–6.

(Z) Takoyaser K., et al. Plastic-coated guide wire for hepatic arteriography. Radiology 1988; 166:545–6.

(AA) Heeney D. Shape your guide wire. AJR 1983; 141:405–6.

(BB) Dawson S., et al. Preserving access during percutaneous catheterization using a double-guide-wire technique. AJR 1983; 141:407.

(CC) Weiser H. C., Ameika J. A. Use of the Amplatz heparin-coated wire guide to facilitate placement of the Hickman catheter. Surg Gynecol Obstet 1985; 160:81–2.

What is claimed is:

1. A guide wire and obturator-catheter system comprising:
    a guide wire comprising flexible helically wound wire including a distal end, an intermediate section and a proximal end and a sufficient length for percutaneous intracorporeal access to a selected body cavity;
    said guide wire including a stop integral with said helically wound wire and defined by a tapered enlarging diameter section including progressively larger loops of said helically wound wire transitioning from said intermediate section to said distal end region thereof;
    an obturator-catheter including a longitudinally extending opening therethrough and an end opening therein of sufficient size to allow the proximal end and intermediate section of said guide wire up to said stop to pass therethrough but of insufficient size to extend toward said distal end of the guide wire beyond said stop;
    whereby said guide wire may be inserted into a body cavity and an obturator-catheter may be inserted into the body cavity over said guide wire with the limit of entrance of the obturator-catheter into the body cavity being determined by said stop.

2. A guide wire and obturator-catheter system in accordance with claim 1 wherein said guide wire includes a visible marking at a predetermined distance from the stop in the direction of said proximal end.

3. A guide wire and obturator-catheter system comprising:
    a guide wire comprising a flexible shelically wound wire including a distal end and a proximal end and a sufficient length for percutaneous intracorporceal access to a selected body cavity;
    the distal end region of said guide wire including a stop and being J shaped with said stop formed from progressively larger loops of said helically wound wire and being located at the end of the body of the J;
    an obturator-catheter including a longitudinally extending opening therethrough and an end opening therein of sufficient size to allow the proximal end and length of said guide wire up to said stop to pass therethrough but of insufficient size to extend toward said distal end of the guide wire beyond said stop;
    whereby said guide wire may be inserted into a body cavity and an obturator-catheter may be inserted into the body cavity with the limit of entrance of the obturator-catheter into the body cavity being determined by said stop.

4. A guide wire for use in percutaneous intracorporeal access to body cavities comprising:
    a flexible helically wound metal wire including a distal end, an intermediate portion and a proximal end;
    said distal end of said guide wire having a greater transverse dimension than said intermediate portion and including an end J shaped portion, the transition region between said distal end and said intermediate portion including progressively larger loops of said wire constituting a stop for objects passing over said guide wire.

5. In a guide wire and obturator/catheter system, an improved obturator comprising:
    an elongated tube having tapered sections at opposite ends thereof including restricted openings therein to allow the passage of a guide wire therethrough with ends extending out of both restricted openings in said tube;
    one of said tapered sections including a trocar;
    said elongated tube being reversible on the guide wire to present said trocar for penetration of tough body tissue and the opposite end for passage through softer tissue.

6. A functional double ended obturator comprising:
    an elongated body;
    a trocar rigidly secured to one end of said elongated body;
    an obturator overlying at least a portion of said trocar obturator and presenting a tapered outer surface over said trocar;
    means biasing said tapered obturator into a normal position overlying said trocar;
    said biasing means being movable responsive to pressure from body tissue on said tapered obturator to retreat said tapered obturator and expose said trocar for penetration of said tissue;
    said body, tapered obturator and trocar including a long internally extending opening therethrough for receiving a guide wire.

7. A functional double ended obturator in accordance with claim 6 wherein said body includes an outer sheath covering said biasing means and at least a portion of said tapered obturator.

8. A functional double ended obturator in accordance with claim 6 including a guide wire having an enlarged distal end stop and a small length of said stop wire;
    the longitudinally opening extending through at least said tapered obturator and said trocar being larger than said length of stop wire and smaller than said enlarged distal end stop.

* * * * *

UNITED STATES PATENT AND TRADEMARK OFFICE
CERTIFICATE OF CORRECTION

PATENT NO.  : 5,059,183

DATED       : 10/22/91

INVENTOR(S) : Neal Semrad

It is certified that error appears in the above-identified patent and that said Letters Patent is hereby corrected as shown below:

Column 5, line 49, delete "10".

Column 5, line 55, delete "15".

Column 9, line 42, change "shelically" to -- , helically--.

Signed and Sealed this

Twenty-third Day of February, 1993

Attest:

STEPHEN G. KUNIN

*Attesting Officer*        Acting Commissioner of Patents and Trademarks